United States Patent [19]

Price et al.

[11] Patent Number: 4,524,071
[45] Date of Patent: Jun. 18, 1985

[54] PYRIMIDONE DERIVATIVES

[75] Inventors: Barry J. Price, Hertford; John W. Clitherow, Sawbridgeworth; John Bradshaw, Ware; Michael Martin-Smith, Ware; Duncan B. Judd, Ware; Roger Hayes, Welwyn, all of England

[73] Assignee: Glaxo Group Limited, London, England

[21] Appl. No.: 58,256

[22] Filed: Jul. 17, 1979

[30] Foreign Application Priority Data

Jul. 26, 1978 [GB] United Kingdom ............... 31153/78

[51] Int. Cl.$^3$ ............... C07D 239/244; A61K 31/505
[52] U.S. Cl. .................................. 514/272; 544/320; 544/321
[58] Field of Search ............... 544/320, 321; 424/251

[56] References Cited

U.S. PATENT DOCUMENTS 4,128,658 12/1978 Price et al. .................. 424/285
4,145,546 3/1979 Brown et al. ................. 544/310
4,154,834 5/1979 Brown ......................... 424/251

FOREIGN PATENT DOCUMENTS 846452 3/1977 Belgium .
3677 2/1978 European Pat. Off. .
1338169 3/1972 United Kingdom .
1419994 4/1974 United Kingdom .

Primary Examiner—Nicholas S. Rizzo
Attorney, Agent, or Firm—Bacon & Thomas

[57] ABSTRACT

Compounds of the formula (I)

$$R_1R_2N\text{-Alk-}Q(CH_2)_nX(CH_2)_mNH-\text{[pyrimidone ring with }R_3, R_4, Y=NH\text{]}$$ (I)

in which
R$_1$ and R$_2$ each may represent hydrogen, alkyl, cycloalkyl, alkenyl, alkynyl, aralkyl, or alkyl, substituted by hydroxy, C$_{1-3}$ alkoxy, amino, C$_{1-3}$ alkylamino or di-C$_{1-3}$ alkylamino or R$_1$ and R$_2$ together with the nitrogen atom to which they are attached form an alicyclic heterocyclic ring which may be unsubstituted or may be substituted by one or more C$_{1-3}$ alkyl groups or a hydroxy group and/or may contain another heteroatom are described.
Alk is a straight lower alkylene chain,
Q is a furan or thiophen ring, the furan ring optionally bearing a further substituent R$_5$ adjacent to the group R$_1$R$_2$NAlk— or Q represents a benzene ring.
R$_5$ represents halogen or C$_{1-3}$ alkyl which may be substituted by a hydroxy or C$_{1-3}$ alkoxy group;
X represents —CH$_2$—, —O— or —S—;
n represents zero or 1;
m represents 2, 3 or 4;
Y represents =O or =S;
R$_3$ represents hydrogen in which case R$_4$ represents methyl or R$_3$ represents —(CH$_2$)$_p$V(CH$_2$)$_q$Ar, phenyl, or alkyl in which case R$_4$ represents hydrogen;
V represents —CH$_2$—, —O—, or —S—;
p represents zero, 1, 2 or 3;
q represents zero, 1, 2 or 3;
the sum of p+q being 3 or less;
Ar represents an aromatic carbocyclic or heterocyclic ring being optionally substituted by at least one C$_{1-3}$ alkyl, C$_{1-3}$ alkoxy C$_{1-3}$ alkyl, hydroxy, C$_{1-3}$ alkoxy, methylenedioxy, halogen, trifluoromethyl or di-C$_{1-3}$ alkylamino group;
except that when n is zero and X is oxygen then Q represents a benzene or thiophen ring. The compounds of formula (I) have pharmacological activity as selective histamine H$_2$-antagonists.

21 Claims, No Drawings

PYRIMIDONE DERIVATIVES

This invention relates to novel pyrimidone derivatives having a selective action on histamine receptors, to processes for the preparation thereof, to pharmaceutical compositions containing them and to their use in therapeutics.

Certain novel heterocyclic derivatives have now been found which are potent and selective $H_2$-antagonists. These compounds, which are more particularly described below, for example show inhibition of the secretion of gastric acid when this is stimulated via histamine receptors (Ash and Schild, Brit. J. Pharmacol. Chemother, 1966, 27, 427). Their ability to do so can be demonstrated in the perfused rat stomach using the method described in German Offenlegungsschrift No. 2,734,070, modified by the use of sodium pentobarbitone (50 mg/kg) as anaesthetic instead of urethane, and in conscious dogs equipped with Heidenhain pouches using the method described by Black et al, Nature 1972 236, 385. Furthermore the compounds antagonise the effect of histamine on the contraction frequency of isolated guinea pig right atrium but do not modify histamine induced contractions of isolated gastro-intestinal smooth muscle which are mediated via $H_1$-receptors.

Compounds with histamine $H_2$-blocking activity may be used in the treatment of conditions where there is a hypersecretion of gastric acid, particularly in gastric and peptic ulceration, as a prophylactic measure in surgical procedures, and in the treatment of allergic and inflammatory conditions where histamine is a known mediator. Thus they may be used for example, either alone or in combination with other active ingredients in the treatment of allergic and inflammatory conditions of the skin.

The present invention provides compounds of the general formula (I)

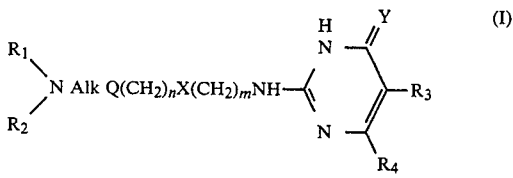

and physiologically acceptable salts, hydrates and bioprecursors thereof, in which $R_1$ and $R_2$ which may be the same or different, each represent hydrogen, alkyl, cycloalkyl, alkenyl, aralkyl alkynyl, or alkyl substituted by hydroxy, $C_{1-3}$ alkoxy, amino, $C_{1-3}$ alkylamino or di-$C_{1-3}$ alkylamino or $R_1$ and $R_2$ together with the nitrogen atom to which they are attached form a 5 to 10 membered alicyclic heterocyclic ring which may be saturated or may contain at least one double bond, may be unsubstituted or may be substituted by one or more $C_{1-3}$ alkyl groups, e.g. methyl, or a hydroxy group and/or may contain another heteroatom, e.g. oxygen or sulphur;

Alk represents a straight alkylene chain of 1–4 carbon atoms;

Q represents a furan or thiophen ring in which incorporation into the rest of the molecule is through bonds at the 2- and 5-positions, the furan ring optionally bearing a further substituent $R_5$ adjacent to the group $R_1R_2N$ Alk or Q represents a benzene ring in which incorporation into the rest of the molecule is through bonds at the 1- and 3- or 1- and 4-positions;

$R_5$ represents halogen e.g. fluorine, chlorine or bromine, or $C_{1-3}$ alkyl which may be substituted by a hydroxy or $C_{1-3}$ alkoxy group;

X represents —$CH_2$—, —O— or —S—;

n represents zero or 1;

m represents 2, 3 or 4;

Y represents =O or =S;

$R_3$ represents hydrogen in which case $R_4$ represents methyl or $R_3$ represents —$(CH_2)_p$ V $(CH_2)_q$ Ar, phenyl or alkyl in which case $R_4$ represents hydrogen;

V represents —CH—, —O— or —S—;

p represents zero, 1, 2 or 3;

q represents zero, 1, 2 or 3;

the sum of P+q being 3 or less;

Ar represents an aromatic carbocyclic or heterocyclic group containing from 5 to 10 ring members, the heterocyclic group containing one or two hetero-atoms selected from nitrogen, oxygen and sulphur and when the aromatic carbocyclic group is phenyl, it being optionally substituted by one or more groups selected from the following: $C_{1-3}$ alkyl, $C_{1-3}$ alkoxy $C_{1-3}$ alkyl, hydroxy, $C_{1-3}$ alkoxy, methylenedioxy, halogen e.g. fluorine, chlorine or bromine, trifluoromethyl and di $C_{1-3}$ alkylamino;

except that when n is zero and X is oxygen then Q represents a benzene or thiophen ring.

The term "alkyl" as a group or part of a group means that the group is straight or branched and has unless otherwise stated preferably 1 to 6 carbon atoms, and in particular 1 to 4 carbon atoms, e.g. methyl or ethyl, and the terms "alkynyl" and "alkenyl" mean that the group has preferably 3 to 6 carbon atoms.

The term "cycloalkyl" means that the group has 3 to 8 carbon atoms The term "aryl" as part of a group preferably means phenyl or a substituted phenyl, for example phenyl substituted with one or more $C_{1-3}$ alkyl or $C_{1-3}$ alkoxy groups or halogen atoms Examples of aromatic carbocyclic and heterocyclic groups for Ar are phenyl, naphthyl , pyridyl, furanyl, thienyl, thiazolyl, oxazolyl, indolyl, quinolyl and isoquinolyl.

The invention includes the compounds of formula (I) in the form of physiologically acceptable salts with inorganic and organic acids. Particularly useful salts include hydrochlorides, hydrobromides and sulphates; acetates, maleates and fumarates. The compounds and their salts may also form hydrates. The compounds of formula (I) can exhibit tautomerism and the formula is intended to cover all tautomers.

The compounds according to the invention, preferably in the form of a salt, may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients.

Thus the compounds according to the invention may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner The compounds of the invention may be formulated for parenteral administration by bolus injection or continuous infusion. Formulations for injection may be presented in unit dosage form in ampoules, or in multidose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glyceride.

For internal administration, a convenient daily dosage regime of the compounds according to the invention would be 1 to 6 doses to the total of some 10 mg to 2 g per day, e.g. 10 mg to 500 mg per day. The precise dosage employed will depend on the size and condition of the patient and on the route of administration.

The compounds according to the invention are, as mentioned above, potent antagonists of histamine at $H_2$-receptors, as is shown by their inhibition of secretion of gastric acid in the perfused rat stomach preparation. Certain compounds for example compounds of formula (I) in which $R_1R_2N$ is $(CH_3)_2N$ or pyrrolidino; Alk is $CH_2$; Ar is 3-pyridyl or 4-pyridyl; Y is oxygen; V is $CH_2$; p and q are both zero; and Q is a furan ring in which case n is 1, m is 2 and X is sulphur, or Q is a benzene ring in which incorporation into the rest of the molecule is through bonds at the 1- and 3-positions in which case n is zero, m is 3 and X is oxygen, are of particular interest since they show a long duration of action in the Heidenhain pouched dog. This long duration of action represents a particular advantage of the compounds of the present invention.

Preferred compounds are those of formula (I) in which:

(1) $R_1R_2N$ represents an alkylamino (e.g. methylamino), dialkylamino (e.g. dimethylamino or ethylmethylamino) group, or a 5 to 7-membered ring without a further heterofunction, e.g. a piperidino or pyrrolidino group;

(2) n is 1, X is sulphur and m is 2 or 3 more particularly 2, or n is 1, X is oxygen and m is 3 or 4, more particularly 3, or n is zero, X is oxygen and m is 3;

(3) Y is oxygen;

(4) $R_4$ is hydrogen and $R_3$ represents the group $(CH_2)p$ V $(CH_2)q$ Ar where p is 0, 1 or 2, V is $CH_2$ or oxygen and q is 0 or 1; more particularly p is 0, q is 0 and V is $CH_2$.

(5) Ar is 2, 3 or 4-pyridyl, phenyl optionally substituted by alkoxy or by dialkylamino, or 3-quinolyl, more preferably Ar is 3 or 4-pyridyl;

(6) Q is furan or 1,3-benzene, more preferably 1,3-benzene, in and Alk is preferably $CH_2$.

Further preferred compounds are those in which Ar is phenyl substituted by $C_{1-3}$ alkoxymethyl in which case preferably p is 2, q is zero and V is oxygen, or those in which Ar is 3-indolyl. Other preferred compounds are those in which $R_3$ is hydrogen and $R_4$ is $CH_3$ or those in which $R_3$ is phenyl and $R_4$ is hydrogen.

Particularly preferred compounds on account of their potency and/or prolonged duration of action are:

2-[[2-[[[5-[(dimethylamino)methyl]-2-furanyl]methyl]thio]ethyl]amino]-5-[(3-pyridinyl)methyl]-4(3H)-pyrimidinone 2-[[2-[[[5-[(dimethylamino)methyl]-2-furanyl]methyl]thio]ethyl]amino]-5-[(4-pyridinyl)methyl]-4(3H)-pyrimidinone 2-[[2-[[[5-[(dimethylamino)methyl]-2-furanyl]methyl]thio]ethyl]amino]-5-[2-[3-(methoxymethyl)-phenoxy]ehtyl]-4(3H)-pyrimidinone 5-[(3-pyridinyl)methyl]-2-[[2-[[[5-[(1-pyrrolidinyl)-methyl]-2-furanyl]methyl]thio]ethyl]amino]-4(3H)-pyrimidinone 2[[3-[[5-[(dimethylamino)methyl]-2-furanyl]methoxy]propyl]amino]-5-[(3-pyridinyl)methyl]-4(3H)-pyrimidinone 2-[[3-[3-[(dimethylamino)methyl]phenoxy]propyl]amino]-5-[(3-pyridinyl)methyl]-4(3H)-pyrimidinone 2-[[3-[3-[(1-pyrrolidinyl)methyl]phenoxy]propyl]amino]-5-[(3-pyridinyl)methyl]-4(3H)-pyrimidinone 5-phenylmethyl-2-[[3-[3-[(1-pyrrolidinyl)methyl]-phenoxy]propyl]amino]-4(3H)-pyrimidinone 2-[[3-[3-[(1-piperidinyl)methyl]phenoxy]propyl]amino]-5-[(3-pyridinyl)methyl]-4(3H)-pyrimidinone and their physiologically acceptable salts.

According to one embodiment the invention provides compounds of the general formula (I) and physiologically acceptable salts, hydrates and bioprecursors thereof, in which $R_1$ and $R_2$, which may be the same or different each represent hydrogen, alkyl, cycloalkyl, alkenyl, aralkyl or alkyl substituted by $C_{1-3}$ alkoxy, $C_{1-3}$ alkylamino or di $C_{1-3}$ alkyl amino, or $R_1$ and $R_2$ together with the nitrogen atom to which they are attached form a saturated monocyclic 5 to 7 membered heterocyclic ring which may contain the further heterofunction —O—;

Alk represents $CH_2$;

$R_3$ represents —$(CH_2)p$ V $(CH_2)q$ Ar and $R_4$ represents hydrogen;

Ar represents an aromatic heterocyclic ring containing from 5 to 10 ring members and containing one or two hetero-atoms selected from N, O and S or Ar represents phenyl which phenyl may be optionally substituted by one or more groups selected from the following: $C_{1-3}$ alkyl, hydroxy, $C_{1-3}$ alkoxy, methylenedioxy, halogen, trifluoromethyl, and di-$C_{1-3}$-alkylamino;

Q, $R_5$, X, V, n,m,p,q and Y are as defined in formula (I);

except that n is not zero when X is oxygen and Q is a furan, substituted furan or thiophen ring and that X is not —$CH_2$— when Q is a furan ring substituted by $R_5$.

The compounds of formula (I) in which Y is =O may be made by reacting a compound of formula (II)

in which $R_1$, $R_2$, Alk, Q and n are as defined in formula (I) and A represents:

—X(CH$_2$)$_m$NH$_2$, hydroxy or —X(CH$_2$)$_m$L' where X and m are as defined in formula (I) and L' is a leaving group, except that when A is hydroxy n must be 1, with an appropriate compound of formula (III)

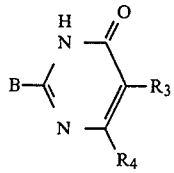
(III)

in which B represents a leaving group L, HX(CH$_2$)$_m$NH— or —NH$_2$, where $R_3$, $R_4$ and m are as defined in formula (I) and X is —O— or —S—. Examples of leaving groups L are thioalkyl and thioaralkyl and examples of leaving groups L' are halogen and acyloxy.

Thus a primary amine of the formula (IV)

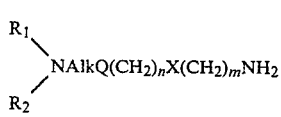
(IV)

in which $R_1$, $R_2$, Alk, Q, X, n and m are as defined in formula (I) may be reacted with a pyrimidone of formula (V)

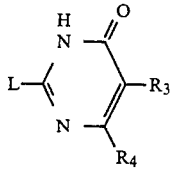
(V)

in which $R_3$ and $R_4$ are as defined in formula (I) and L is a leaving group, for example thioalkyl or thioaralkyl, e.g. thiomethyl.

The reaction can be carried out with or without a solvent. Suitable solvents include alcohols, e.g. ethanol, and acetonitrile or the amine (IV) can act as a solvent. The reaction is preferably carried out at elevated temperature.

In another embodiment of this process a compound of formula (VI)

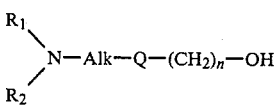
(VI)

in which $R_1$, $R_2$, Alk and Q are as defined in formula (I) and n is 1, may be reacted with a compound of formula (VII)

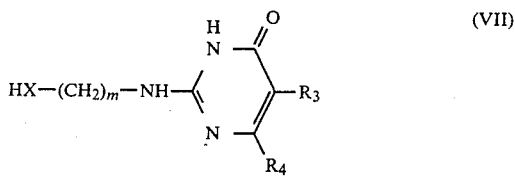
(VII)

in which X is S or O and m, $R_3$ and $R_4$ are as defined in formula (I). The reaction can be carried out by reacting the compounds (VI) and (VII) directly in the presence of an acid such as methane sulphonic acid or a mineral acid such as concentrated hydrochloric acid.

In a third embodiment of this process a compound of formula (VIII)

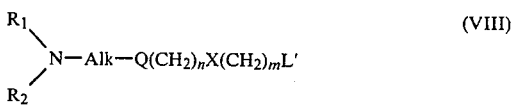
(VIII)

in which $R_1$, $R_2$, Alk, Q, X, n and m are as defined in formula (I) and L' is a leaving group, such as halogen e.g. chlorine, or acyloxy e.g. acetyloxy, may be reacted with a compound of formula (IX)

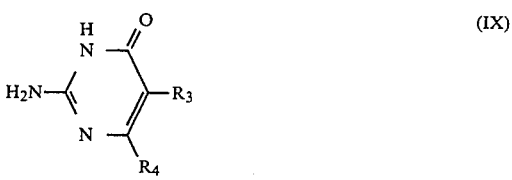
(IX)

in which $R_3$ and $R_4$ are as defined in formula (I).

The compounds of formula (I) in which Y is oxygen may also be made by reacting a guanidine of formula (X)

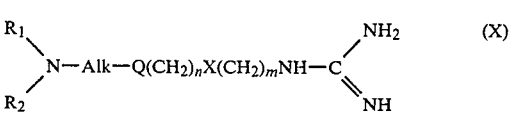
(X)

in which $R_1$, $R_2$, Alk, Q, X, n and m are as defined in formula (I), with a compound of formula (XI)

(XI)

in which $R_3$ and $R_4$ are as defined in formula (I) and $R_6$ is alkyl, (e.g. ethyl), benzyl or phenyl.

The reaction can be carried out by heating the guanidine of formula (X) together with the compound of formula (XI), optionally in a solvent such as the alcohol corresponding to the ester function in compound (XI) i.e. $R_6$OH, at elevated temperature, preferably in the presence of base, e.g. the sodium alkoxide corresponding to the ester function in compound (XI) i.e. $R_6$ONa.

Compounds of formula (I) in which Y is sulphur may be prepared by reacting a compound of formula (I) in which Y is oxygen with phosphorus pentasulphide. The reaction may be carried out in a solvent such as pyridine at elevated temperature.

Where $R_1$ and $R_2$ are both hydrogen in intermediates in any of the above reactions, the primary amino function may be protected, for example as a phthalimido group. The protecting group may be removed at any suitable stage. In the case of a phthalimido group this may be cleaved using a primary amine, e.g. methylamine, or a hydrazine, e.g. hydrazine hydrate.

The amines of formula (IV) may be prepared as described in German Offenlegungsschrifts Nos. 2,734,070, 2,821,409 and 2,821,410 and in British published application No. 2006771, or by methods analogous to those described in these documents.

The intermediates of formula (X) may be made by treating an amine of formula (IV) with a compound of formula (XII)

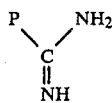
(XII)

where P is a leaving group e.g. thiomethyl or 3,5-dimethylpyrazole.

The intermediates of formula (VII) may be made from those of formula (V) by reaction with an ω-aminoalkylthiol or ω-aminoalkanol.

The pyrimidones of formula (V) in which L is thioalkyl may be made by treating the corresponding thiol (L in formula (V) is SH) with an alkylating agent e.g. an alkylhalide or dialkylsulphate. The thiols can be made from compounds of formula (XI) by treatment with thiourea. Alternatively the pyrimidones of formula (V) in which L is thioalkyl may be prepared by treating the compounds of formula (XI) with the appropriate S-alkyl isothiouronium salt, e.g. S-methyl isothiouronium sulphate.

Where the product of any of the above processes is a free base and a salt is required, the salt may be formed in a conventional manner. Thus, for example, a generally convenient method of forming the salts is to mix appropriate quantities of the free base and the acid in an appropriate solvent(s), e.g. an alcohol such as ethanol or an ester such as ethyl acetate.

The invention is illustrated by the following examples.

EXAMPLE 1

(i)

2-[[2-[[[5-[(Dimethylamino)methyl]-2-furanyl]methyl]thio]ethyl]amino]-5-(phenylmethyl)-4(3H)-pyrimidinone, bismaleate 5-[[(2-Aminoethyl)thio]methyl]-N,N-dimethyl-2-furanmethanamine (4.28 g) and 2-(methylthio)-5-(phenylmethyl)-4 (3H)-pyrimidinone (2.32 g) were heated at 140° for 5 hours. The residue, after column chromatography (silica/ethylacetate) gave an oil which was dissolved in ethyl acetate (50 ml) and treated with maleic acid (1.46 g) in methanol (25 ml). After partial evaporation of the solution, the title compound was obtained as white prisms (2.9 g) m.p. 145°–146°.

Analysis Found: C, 54.9; H, 5.4; N, 8.9; $C_{21}H_{26}N_4O_2S \cdot 2C_4H_4O_4$ requires: C, 55.2; H, 5.4; N, 8.9%

Similarly prepared were:

(ii)

2-[[2-[[[5-[(Dimethylamino)methyl]-2-furanyl]methyl]thio]ethyl]amino]-5-[(2-pyridinyl)methyl]-4-(3H)-pyrimidinone (0.93 g) as an amber oil from 2-[[(aminoethyl)thio]methyl]-N,N-dimethyl-2-furanmethanamine (2 g) and 2-(methylthio)-5-[(2-pyridinyl)methyl]-4(3H)-pyrimidinone (1.07 g) at 140° for 4 hours, followed by column chromatography (silica/methanol -0.88 ammonia, 79:1).

T.L.C. (silica/methanol - 0.88 ammonia, 79:1) Rf.0.4.

Analysis: Found: C, 59.4; H, 6.6; N, 16.6; $C_{20}H_{25}N_5O_2S \cdot \frac{1}{3}H_2O$ requires C, 59.2; H, 6.4; N, 17.3%.

(iii)

2-[[2-[[[5-[(Dimethylamino)methyl]-2-furanyl]methyl]thio]ethyl]amino]-5-[(3-pyridinyl)methyl]-4(3H)-pyrimidinone (1.6 g), m.p. 128°–129° from 5-[[(2-aminoethyl)thio]methyl]-N,N-dimethyl-2-furanmethanamine (2.5 g) and 2-(methylthio)-5- (3-pyridinyl)methyl]-4(3H)-pyrimidinone (1.5 g) at 140° for 3 hr. followed by crystallisation from ethyl acetate/light petroleum (b.p. 60°–80°.

T.L.C. (silica/methanol - 0.88 ammonia, 79:1) Rf. 0.53.

(iv)

2-[[2-[[[5-[(Dimethylamino)methyl]-2-furanyl]methyl]thio]ethyl]amino]-5-[(4-pyridinyl)methyl]-4(3H)-pyrimidinone (0.77 g) as an amber oil from 5-[[(2-aminoethyl)thio]methyl]-N,N-dimethyl-2-furanmethanamine (0.76 g) and 2-(methylthio)-5-[(4-pyridinyl)methyl]-4(3H)-pyrimidinone (0.75 g) at 120° for 4 hr. followed by column chromatography (silica/methanol 0.88 ammonia, 79:1).

T.L.C. (silica/methanol - 0.88 ammonia, 79:1) Rf. 0.44.

Analysis Found: C, 56.8; H, 6.5; N, 16.6; $C_{20}H_{25}N_5O_2S \cdot 1\frac{1}{4}H_2O$ requires C, 56.9; H, 6.6; N, 16.6%.

(v)

5-[(3-Pyridinyl)methyl]-2-[[2-[[[5-[(1-pyrrolidinyl)methyl]-2-furanyl]methyl]thio]ethyl]amino]-4(3H)-pyrimidinone (0.83 g) as an amber oil from 2-[[[5-[(1-pyrrolidinyl)methyl]-2-furanyl]methyl]thio]ethanamine (1.1 g) and 2-(methylthio)-5-[(3-pyridinyl)methyl]-4(3H)-pyrimidinone (1 g) at 140° for 4 hr. followed by column chromatography (silica/methanol -0.88 ammonia, 79:1).

T.L.C. (silica/methanol - 0.88 ammonia, 79:1) Rf. 0.55.

Analysis, Found: C, 61.0; H, 6.5; N, 15.9. $C_{22}H_{27}N_5O_2S \cdot \frac{1}{4}H_2O$ requires C, 61.4; H, 6.5; N, 16.3%.

(vi)

2-[[2-[[[5-[(Dimethylamino)methyl]-2-furanyl]methyl]thio]ethyl]amino]-5-[4-methoxyphenyl)methyl]-4(3H)-pyrimidinone (1.3 g), m.p. 86°–87° from 5-[[(2-aminoethyl)thio]methyl]-N,N-dimethyl-2-furanmethanamine (2.14 g) and 5-[(4-methoxyphenyl)methyl]-2-(methylthio)-4(3H)-pyrimidinone (1.31 g) at 140° for 4 hr. followed by column chromatography (silica/methanol) and crystallisation from ethyl acetate - light petroleum (b.p. 60°–80°.)

T.L.C. (silica/methanol) Rf. 0.37.

(vii)

2-[[2-[[[5-[(Dimethylamino)methyl]-2-furanyl]methyl]thio]ethyl]amino]-5-methyl-4(3H)-pyrimidinone (2.57 g), m.p. 86°–89° from 5-[[(2-aminoethyl)thio]methyl]-N,N-dimethyl-2-furanmethanamine (4.15 g) and 5-methyl-2(methylthio)-4(3H)-pyrimidinone (2 g) at 140° for 4 hr. followed by column chromatography (silica/methanol) and solidification from ether.

T.L.C. (silica/methanol) Rf. 0.34.

(viii)

5- (4-Chlorophenyl)methyl -2-[[2-[[[5-[(dimethylamino)methyl]-2-furanyl]methyl]thio]ethyl]amino]-4(3H)-pyrimidinone (1.25 g), m.p. 118°–120° from 5-[(2-aminoethyl)thio]methyl]-N,N-dimethyl-2-furanmethanamine (2.14 g) and 5-[(4-chlorophenyl)methyl]-2-(methylthio)-4(3H)-pyrimidinone (1.33 g) at 140° for 4 hr. followed by column chromatography (silica/ethylacetate-methanol, 1:1) and crystallisation from methyl acetate - light petroleum (b.p. 60°–80°).

T.L.C. (silica/methanol) Rf. 0.47.

(ix)

2-[[2-[[[5-[(Dimethylamino)methyl]-2-furanyl]methyl]thio]ethyl]amino]-6-methyl-4(3H)-pyrimidinone (2.86 g) as a yellow oil from 5-[[(2-aminoethyl)thio]methyl]-N,N-dimethyl-2-furanmethanamine (2.14 g) and 6-methyl-2-(methylthio)-4(3H)-pyrimidinone (1.5 g) at 120° for 4 hr. followed by column chromatography (silica/methanol).

T.L.C. (silica/methanol - 0.88 ammonia, 79:1) Rf. 0.5.

Analysis, Found: C, 53.7; H, 6.7; N, 16.6. $C_{15}H_{22}N_4O_2S.\frac{3}{4}H_2O$ requires C, 53.6; H, 7.1; N, 16.7%.

(x)

2-[[3-[[5- (Dimethylamino)methyl]-2-furanyl]methoxy]propyl]amino]-5-[(3-pyridinyl)methyl]-4(3H)-pyrimidinone (0.57 g) as a yellow oil from 5- (3-aminopropoxy)methyl]-N,N-dimethyl-2-furanmethanamine (1 g) and 2-(methylthio)-5-[(3-pyridinyl)methyl]-4(3H)-pyrimidinone (1 g) at 140° for 6 hr. followed by colun chromatography (silica/methanol).

T.L.C. (silica/methanol - 0.88 ammonia, 79:1) Rf. 0.45.

Analysis, found: C, 61.9; H, 6.9; N, 16.8; $C_{21}H_{27}N_5O_3.\frac{1}{2}H_2O$ requires: C, 62.1; H, 6.9; N, 17.2%.

(xi)

2-[[2-[[[5-[(Dimethylamino)methyl]-4-methyl-2-furanyl]methyl]thio]ethyl]amino]-5-(3-pyridinyl)methyl]-4(3H)-pyrimidinone (0.58 g) m.p. 138°–139° from 5-[[(2-aminoethyl)thio]methyl-3-methyl-N,N-dimethyl-furanmethanamine (1 g) and 2-(methylthio)-5-[(3-pyridinyl)methyl- 4(3H)-pyrimidinone (0.8 g) at 140° for 3 hr. followed by column chromatography (silica/methanol) and crystallisation from methyl acetate.

T.C.L. (silica/methanol - 0.88 ammonia, 79:1) Rf. 0.5.

(xii)

2-[[2-[[[5-[(Methylamino)methyl]-2-furanyl]methyl]thio]ethyl]amino]-5-[(3-pyridinyl)methyl]-4-(3H)-pyrimidinone (0.53 g) as a brown oil from 5-[[(2-aminoethyl)thio]methyl]-N-methyl-2-furanmethanamine (0.7 g) and 2-(methylthio)-5-[(3-pyridinyl)methyl]-4-(3H)-pyrimidinone (0.75 g) at 140° for 3 hours at 180° for 30 minutes followed by column chromatography (silica/methanol-0.88 ammonia 79:1).

TLC (Silica/methanol-0.88 ammonia 79:1) Rf 0.4.

Analysis Found: C, 57.7; H, 6.2; N, 17.6; $C_{19}H_{23}N_5O_2S.\frac{1}{2}H_2O$ requires: C, 57.9; H, 6.1; N, 17.8%.

EXAMPLE 2

(i)

2-[[3-[3-[(Dimethylamino)methyl]phenoxy]propyl]amino]-5- (3-pyridinyl)methyl-4 (3H)-pyrimidinone 3-(3-Aminopropoxy)-N,N-dimethylbenzenemethanamine (0.98 g) and 2-(methylthio)-5-[(3-pyridinyl)methyl]-4(3H)-pyrimidinone (1 g) were heated at 140° for 16 h. The residue, after column chromatography (silica/methanol -0.88 ammonia, 79:1) gave the title compound as a yellow gum (0.96 g).

T.L.C. (silica/methanol - 0.88 ammonia, 79:1) Rf. 0.34.

Analysis, Found: C, 65.9, H, 6.8; N, 17.2; $C_{22}H_{27}N_5O_2.\frac{1}{2}H_2O$ requires C, 65.7, H, 7.0; N, 17.4%.

Similarly prepared were:

(ii)

2-[[3-[3-(1-Pyrrolidinyl)methyl]phenoxy]propyl]amino]-5-[(3-pyridinyl)methyl]-4(3H)-pyrimidinone (1.3 g) as a pale yellow gum irom 3-[3-[(1-pyrrolodinyl)methyl]phenoxy]propanamine (1.4 g) and 2-(methylthio)-5-(3-pyridinyl)methyl]-4(3H)-pyrimidinone (1 g) at 150° for 2.5 h. followed by column chromatography (silica/methanol - 0.88 ammonia, 79:1).

T.L.C. (silica/methanol - 0.88 ammonia, 79:1) Rf. 0.36.

Analysis, Found: C, 68.5; H, H, 7.1; N, 16.7; $C_{24}H_{29}N_5O_2$ requires: C, 68.7; H, 7.0; N, 16.7%.

(iii)

5-Phenylmethyl-2-[3-[3-[(1-pyrrolidinyl) methyl]phenoxy]propyl]amino]-4(3H)-pyrimidinone (1.66 g) as a yellow oil from 3-[3-[(1-pyrrolidinyl)methyl]phenoxy]propanamine (1.7 g) and 2-(methylthio)-5-(phenylmethyl)-4(3H)-pyrimidinone (1.16 g) at 150° for 2 h. followed by column chromatography (silica/methanol).

T.L.C. (silica)methanol - 0.88 ammonia, 79:1) Rf. 0.33.

Analysis, Found: C, 70.2; H, 7.4; N, 12.9; $C_{25}H_{30}N_4O_2.\frac{1}{2}H_2O$ requires: C, 70.2; H, 7.3; N, 13.1%.

(iv)

2-[[3-[3-[(1-Piperidinyl)methyl]phenoxy]propyl]amino]-5-[(3-pyridinyl)methyl]-4(3H)-pyrimidinone (0.94 g) as a yellow oil from 3-[3-[(1-piperidinyl)methyl]phenoxy]propanamine (1.3 g) and 2-(methylthio)-5-[(3-pyridinyl) methyl]-4(3H)-pyrimidinone (0.6 g) at 135° for 4 h. followed by column chromatography (silica/methanol - 0.88 ammonia, 79:1).

T.L.C. (silica/methanol - 0.88 ammonia, 79:1) Rf. 0.54.

Analysis, Found: C,69.6; H, 7.3; N, 16.2; $C_{25}H_{31}N_5O_2$ requires: C, 69.3; H, 7.2; N, 16.2%.

(v)

2-[[3-L3-[(Dimethylamino)methyl]phenoxy]propyl]amino]-6-methyl-4(3H)-pyrimidinone. (2.01 g), m.p. 113.5°–114.5° from 3-(3-aminopropoxy)-N,N-dimethylbenzenemethanamine (2.25 g) and 6-methyl-2-(methylthio)-4(3H)-pyrimidinone (1.5 g) at 130° for 5 h. followed by column chromatography (silica/methanol) and crystallisation from ethyl acetate.

T.L.C. (silica/methanol) Rf. 0.21.

(vi)

2-[[2-[[[3-[(1-piperidinyl)methyl]phenyl]methyl]thio]ethyl]amino]-5-[(3-pyridinyl)methyl]-4(3H)-pyrimidinone (0.9 g) m.p. 142.5°-144° from 2-[[[3-[(1-piperidinyl)methyl]phenyl]methyl]thio]ethanamine (0.81 g) and 2-(methylthio)-5-[(3-pyridinyl)methyl]-4-(3H)-pyrimidinone (0.65 g) at 100° for 6 hours and 140° for 2 hours followed by column chromatography (silica/methanol) and trituration of the product with ether. TLC (silica/methanol) Rf. 0.26.

(vii)

2-[[3-[4-[2-(dimethylamino)ethyl]phenoxy]propyl]amino]-5-[(3-pyridinyl)methyl]-4(3H)-pyrimidinone (0.4 g) as a pale brown oil from 4-(3-aminopropoxy)-N,N-dimethylbenzineethanamine (0.6 g) and 2-(methylthio)-(5-[(3-pyridinyl)methyl]-4(3H)-pyrimidinone (0.6 g) at 160°-180° for 16 hours followed by column chromatography (silica/Methanol—0.88 ammonia, 79:1).

TLC (Silica/methanol - 0.88 ammonia) Rf 0.2.

NMR $\tau$ (CDCl$_3$) - 0.6 (1H, br, NH); 1.55 (d, CH), 1.68 (dd, CH) (2H); 2.54 (m, CH), 2.57 (s, CH) (2H); 2.80 - 3.10 (4H, m 3CH and NH), 3.27 (2H, ½AA'BB', 2CH), 6.10 (2H, t, CH$_2$), 6.50 (4H, s and m, 2CH$_2$), 7.20-7.70 (4H, AA'BB', 2CH$_2$), 7.77 (6H, s, 2CH$_3$), 8.05 (2H, m, CH$_2$).

EXAMPLE 3

2-[[2-[[[5-[(Dimethylamino]methyl]-2-furanyl]methyl]thio]ethyl]amino]-5-[2-[3-(methoxymethyl)phenoxy]ethyl]-4(3H)-pyrimidinone

A. 4-(3-Formylphenoxy)butyric acid, ethyl ester

A mixture of 4-bromobutyric acid, ethyl ester (19.5 g), m-hydroxybenzaldehyde (12.2 g) and anhydrous potassium carbonate (27.6 g) in dimethylformamide (150 ml) was stirred for 12 hr. at room temperature. The suspension was filtered, the filtrate evaporated in vacuo water (100 ml) added and the suspension extracted with ether. The ethereal extract was washed with 2 N sodium hydroxide (100 ml) then brine (50 ml) and dried (MgSO$_4$). Evaporation of the ether gave an oil which was distilled 175°-185°/0.1 mm to give the title compound 19.1 g).

T.L.C. (silica/light petroleum b.p. 60°-80° -ethyl acetate, 3:1) Rf. 0.33.

N.M.R. $\tau$ (CDCl$_3$) 2.40-3.00 (4H, m, 4CH), -0.80 (1H, s, CHO); 5.80(q,CH$_2$), 5.90(t,CH$_2$) (4H); 7.30-8.00(4H, m, 2CH$_2$), 8.72(3H, t,CH$_3$).

B. 4-[3-(Methoxymethyl)phenoxy]butyric acid, methyl ester

A solution of 4-(3-formylphenoxy)butyric acid, ethyl ester (4.72 g) in methanol (25 ml) containing hydrogen chloride (0.35 g) was stirred for 12 hr. at room temperature, then cooled to 0°. Sodium cyanoborohydride (1.26 g) was added and after 30 min., iced water (200 ml) was added and the mixture extracted with ether (2×150 ml). Evaporation of the dried (MgSO$_4$) ethereal extracts gave a pale yellow oil which was distilled (165°/0.8 mm) to give the title compound (3.8 g).

T.L.C. (silica/light petroleum, b.p. 60°-80° -ethyl acetate, 3:1) Rf. 0.47.

N.M.R. $\tau$ (CDCl$_3$) 2.70 (1H, m, CH), 2.90-3.30 (3H, m, 3CH), 5.53(2H, s, CH$_2$), 5.94(2H, t, CH$_2$), 6.28(3H, s, CH$_3$), 6.59(3H, s, CH$_3$), 7.20-8.10 (4H, m, 2CH$_2$).

C. 2-Mercapto-5-[2-[3-(methoxymethyl)phenoxy]ethyl]-4(3H)-pyrimidinone

A solution of 4-[3-(methoxymethyl) phenoxy]butyric acid, methyl ester (6 g) and ethylformate (2.05 g) in dry ether (50 ml) was added slowly to a stirred suspension of sodium (0.58 g) in dry ether (50 ml) containing ethanol (0.1 ml). After 4 days, the solvent was evaporated and a solution of the residue and thiourea (2.1 g) in ethanol (50 ml) heated under reflux for 12 hr. The solvent was evaporated the residue dissolved in water (20 ml) and acidified with acetic acid. The suspension was extracted with ethyl acetate (2×50 ml) and the combined extracts dried (Na$_2$SO$_4$). Evaporation of the solvent gave an oil which was chromatographed (silica/ethyl acetate - light petroleum, b.p. 60°-80°, 1:1) to give the title compound (1 g), m.p. 117°-119°.

T.L.C. (silica/ethyl acetate - light petroleum, b.p. 60°-80°, 1:1) Rf. 0.59.

D. 5-[2-[3-(Methoxymethyl)phenoxy]ethyl]-2-(methylthio)-4(3H)-pyrimidinone

Dimethyl sulphate (0.363 g) was added to a stirred solution of 2-mercapto-5-[2-[3-(methoxymethyl)phenoxy]ethyl]-4(3H)-pyrimidinone (0.85 g) in water (20 ml) and potassium hydroxide (0.163 g). After 1 h., the suspension was filtered to give the title compound (0.76 g) m.p. 129°-131°.

T.L.C. (silica/light petroleum, b.p. 60°-80° ethylacetate, 1:1) Rf. 0.63.

E. 2-[[2-[[[5-[(Dimethylamino)methyl]-2-furanyl]methyl]thio]ethyl]amino]-5-[2-[3-(methoxymethyl)phenoxy]ethyl]-4(3H)-pyrimidinone A mixture of 5-[2-[3-(methoxymethyl)phenoxy]ethyl]-2-(methylthio)-4(3H)-pyrimidinone (0.7 g ) and 5-[[(2-aminoethyl)thio]methyl]-N,N-dimethyl-2-furanmethanamine (0.54 g) was heated at 140° for 2 h. The residue was chromatographed (silica/methanol) to give the title compound (0.55 g) as a pale yellow oil.

T.L.C. (silica/methanol) Rf. 0.31.

Analysis, Found: C, 59.6; H, 6.9; N, 11.3; C$_{24}$H$_{32}$N$_4$O$_4$½H$_2$O requires: C, 59.9; H, 6.9; N, 11.6%.

EXAMPLE 4

2-[[2-[[[5-[(Dimethylamino)methyl]-2-furanyl]methyl]thio]ethyl]amino]-5-(3-pyridinyloxy)-4(3H)-pyrimidinone

A. 2-(3-Pyridinyloxy)acetic acid, ethyl ester

Sodium hydride (7.15 g) was added portion-wise to a stirred solution of 3-hydroxypyridine (19 g) in dry dimethylsulphoxide (100 ml) during 1 hr. Ethyl bromoacetate (33.4. g) was added during 1 h. and water (250 ml) slowly added. The solution was extracted with chloroform (3×150 ml) and the combined extracts washed with 2 N sodium carbonate (75 ml) and dried (Na$_2$SO$_4$). Evaporation of the solvent gave a liquid which was distilled (120°-130°/0.1 mm) to yield the title compound (8.7 g).

T.L.C. (silica/diethyl ether) Rf. 0.35.

N.M.R. $\tau$ (CDCl$_3$) 1.60-1.80(2H, m, 2CH), 2.70-2.80(2H, m, 2CH), 5.30(2H, s, CH$_2$), 5.68 (2H, q, CH$_2$), 8.72 (3H, t, CH$_3$).

B.
1,2-Dihydro-5-(3-pyridinyloxy)-2-thioxo-4-(3H)-pyrimidinone

To a stirred suspension of finely powdered sodium (1.18 g) in dry ether (50 ml) was added ethyl formate (4.2 g) and 2-(3-pyridinyloxy)acetic acid, ethyl ester (8.5 g) in dry ether (50 ml) during 2 h. After 12 h. the ether was evaporated, the residue dissolved in ethanol (100 ml), thiourea (4.31 g) added and the mixture refluxed for 7 h. After evaporation of the solvent, the residue was dissolved in water (50 ml) and the solution adjusted to pH 5.5 with acetic acid. The precipitated solid was crystallised from isopropanol to give the title compound (4.4 g) m.p. 227°-230°. T.L.C. (silic/ethyl acetate) Rf. 0.38.

C.
2-(Methylthio)-5-(3-pyridinyloxy)-4(3H)-pyrimidinone

Methyl iodide (1.48 g) was added to a stirred solution of 1 2-dihydro-5-(3-pyridinyloxy)-2-thioxo-4(3H)-pyrimidinone (2.21 g) and potassium hydroxide (0.56 g) in ethanol (10 ml) and water (5 ml) at 60°. After heating at 98°-100° for 30 min., the solid which separated on cooling was crystallised from propan-2-ol to give the title compound (1.5 g), m.p. 205°-208°.

T.L.C. (silica/ethyl acetate) Rf. 0.27.

D. 2-[[2-[[[5-[(Dimethylamino)methyl]-2-furanyl]methyl]thio]ethyl]amino]-5-(3-pyridinyloxy)-4(3H)-pyrimidinone A mixture of 2-(methylthio)-5-(3-pyridinyloxy)-4(3H)-pyrimidinone (1.18 g) and 5-[[(2-aminoethyl)thio]methyl]-N,N-dimethyl-2-furanmethanamine (2.14 g) was heated at 140° for 6 h. the residue was chromatographed (silica/ethyl acetate-methanol, 1:1) to give the title compound (1.0 g) as a yellow gum.

T.L.C. (silica/methanol) Rf. 0.33.

Analysis, Found: C, 54.8; H, 5.8; N, 16.5; $C_{19}H_{23}N_5O_3S \cdot H_2O$ requires: C, 54.4; H, 6.0; N, 16.7%.

EXAMPLE 5
2-[[2-[[[5-[(Dimethylamino)methyl]-2-furanyl]methyl]thio]ethyl]amino[5-[[4-(dimethylamino)phenyl]methyl]-4(3H)-pyrimidinone

A.
5-[[-(Dimethylamino)phenyl]methyl]-1,2-dihydro-2-thioxo-4(3H)-pyrimidinone To a stirred suspension of finally divided sodium (1.86 g) in dry ether (50 ml) was added a mixture of 3-[(4-dimethylamino)phenyl]propanoic acid ethyl ester (17 g) and ethyl formate (6.26 g) in dry ether (50 ml) during 2 h. After 12 h., evaporation of the solvent gave a solid which was refluxed with thiourea (6.43 g) in ethanol (100 ml) for 6 h. Evaporation of the solvent gave a solid which was dissolved in water (50 ml) and acidified with acetic acid. The precipitate was extracted with ethyl acetate (2×250 ml), the extracts dried (Na₂SO₄) and evaporated. The residue was chromatographed (silica/ethylacetate-light petroleum, b.p. 60°-80°, 1:1) and the product crystallised from ethylacetate-cyclohexane to give the title compound (4.6 g), m.p. 208°-211°.

T.L.C (silica/ethyl acetate-light petroleum, b.p. 60°-80°, 1:1). Rf. 0.29.

B.
5-[[4-(Dimthylamino)phenyl]methyl]-2-(methylthio)-4(3H)-pyrimidinone

A solution of methyl iodide (0.29 ml) in methanol (10 ml) was slowly added to a solution of 5-[[4-(dimethylamino)phenyl]methyl]-1,2-dihydro-2-thioxo-4(3H)-pyrimidinone (1.1 g) and 2 N hydrochloric acid (3 ml) in water (5 ml) at 60°. The solution was heated at 98°-100° for 2 h., cooled to 5° and 2 N sodium carbonate (4 ml) added slowly. The solid was filtered off and crystallised from methanol to give the title compound (0.7 g), m.p. 215°-218°.

T.L.C. (silica/ethyl acetate) Rf. 0.43.

C.
2-[[2-[[[5-[(Dimethylamino)methyl]-2-furanyl]methyl]thio]ethyl]amino]-5-[[4-(dimethylamiho)phenyl]methyl]-4(3H)-pyrimidinone A mixture of 5-[[4-(dimethylamino) phenyl]methyl]-2-(methylthio)-4(3H)-pyrimidinone (0.68 g) and 5-[[(2-aminoethyl)thio]methyl]-N,N-dimethyl-2-furanmethanamine (1.07 g) was heated at 140° for 2 h. and the residue chromatographed (silica/methanol-ethyl acetate, 1:1) to give an oil. This was solidified under light petroleum (b.p. 60°-80°) yielding the title compound (0.95 g).

T.L.C. (silica/methanol) Rf. 0.31.

Analysis, Found: C, 61.6; H, 7.2; N, 15.7; $C_{23}H_{31}N_5O_2S \cdot \frac{1}{2}H_2O$ requires C, 61.3; H, 7.2; N. 15.5%.

EXAMPLE 6
2-[[4-[[5-[(Dimethylamino)methyl]-2-furanyl]methoxy]butyl]amino]-5-[(3-pyridinyl)methyl]-4(3H)-pyrimidinone

A. 5-[(4-Aminobutoxy methyl-N,N-dimethyl-2-furanmethanamine

A solution of methanesulphonic acid (86 g), 5-[(dimethylamino)methyl]-2-furanmethanol (15.52 g), and 4-aminobutanol (17.82 g) in tetrahydrofuran (100 ml) was heated at 98°-100° for 1.5 h. After 1 h. at room temperature, excess anhydrous sodium carbonate was added and the suspension filtered after 18 h. The filtrate was evaporated, water (230 ml) added and the suspension extracted with ether (3×80 ml). The ethereal extracts were washed with water (2×50 ml), the aqueous fraction acidified with oxalic acid (25 g) and evaporated to low bulk. Excess anhydrous sodium carbonate and ethyl acetate (200 ml) were added, the suspension heated at boiling for 30 min. and the suspension filtered after 2 h. Evaporation of the filtrate yielded an oil which was distilled (100°-110°/0.08 mm) to give the title compound (6.64 g).

T.L.C. (silica/methanol - 0.88 ammonia 19:1) Rf 0.3.

Analysis, Found: C, 63.6; H 10.1 N, 12.1; $C_{12}H_{22}N_2O_2$ requires C, 63.7 H 9.8 N, 12.4%.

B.
2-[[4-[[5-(Dimethylamino)methyl]-2-furanyl]methoxy]butyl]amino]-5[(3-pyridinyl)methyl]-4(3H)-pyrimidinone A mixture of 5-[(4-aminobutoxy)methyl]-N,N-dimethyl-2-furanmethanamine (1 g) and 2-methylthio)-5-[(3-pyridinyl)methyl]-4(3H)-pyrimidinone (1 g) was heated at 140° for 7 h. Column chromatography (silica/methanol) of the residue yielded the title compound (0.95 g) as a yellow oil.

T.L.C. (silica/methanol) Rf. 0.25.

Analysis, Found: C, 62.6; H, 7.4; N, 16.3; $C_{22}H_{29}N_5O_3\frac{1}{2}H_2O$ requires C, 62.8; H, 7.2; N, 16.7%.

EXAMPLE 7

2-[[2-[[[5-[(Dimethylamino)methyl]-2-furanyl]methyl]-thio]ethyl]amino]-5-[(3-quinolinyl)methyl]-4(3H)-pyrimidinone

A. 3(3-Quinolinyl)propanoic acid, ethyl ester

A solution 3-(3-quinolinyl)propanoic acid (4.4 g) and concentrated sulphuric acid (2 ml) in absolute ethanol (50 ml) was refluxed for 5 h. then, evaporated to dryness. Aqueous sodium bicarbonate (8%, 50 ml) was added, the mixture extracted with ether (2×100 ml) and the ethereal extracts dried (Na$_2$SO$_4$). Evaporation of the ether and distillation of the residual oil (150°/0.06 mm) gave the title compound (4.3 g).

T.L.C. (silica/ethyl acetate) Rf. 0.59.

N.M.R. τ (CDCl$_3$). 1.18(1H, d, CH); 1.80–2.60 (5H, m, 5CH), 5.85(2H, q, CH$_2$), 6.85(2H, AA'BB', CH$_2$), 7.17(2H, AA'BB', CH$_2$), 8.78 (3H, t, CH$_3$).

B. 1,2-Dihydro-5-[(3-quinolinyl)methyl]-2-thioxo-4(3H)-pyrimidinone

To a stirred suspension of finely powdered sodium (0.44 g) in dry ether (50 ml) was added a mixture of 3-(3-quinolinyl) propanoic acid, ethyl ester (4.2 g) and ethyl formate (1.42 g) in dry ether (50 ml) during 1 h. After refluxing for 1 h., the ether was evaporated and a solution of the residue and thiourea (1.46 g) in ethanol (50 ml) was refluxed for 18 h. After evaporation of the ethanol, the residue was dissolved in water (50 ml) and the solution acidified with acetic acid. The precipitated solid was crystallised from ethanol to give the title compound (1.35 g), m.p. 290°–292°.

T.L.C. (silica/ethylacetate) Rf. 0.44.

C. 2-(Methylthio)-5-[(3-quinolinyl)-methyl]-4(3H) pyrimidinone

Methyl iodide (0.56 g) was added to a stirred solution of 1,2-dihydro-5-[(3-quinolinyl)methyl]-2-thioxo-4(3H)-pyrimidinone (1.2 g) and potassium hydroxide (0.23 g) in aqueous ethanol (50%, 20 ml) at 60°. After 30 min., the solution was cooled and the solid which separated was crystallised from aqueous ethanol to give the title compound (1.1 g), m.p. 220°–221°.

T.L.C. (silica/ethyl acetate) Rf. 0.48.

D. 2-[[2-[[[5-(Dimethylamino)methyl]-2-furanyl]methyl]-thio]ethyl]amino]-5-[(3-quinolinyl)methyl]-4(3H)-pyrimidinone A mixture of 2-(methylthio)-5- (3-quinolinyl)methyl]-4-(3H)-pyrimidinone (1 g) and 5-[[(2-aminoethyl)thio]-methyl]-N,N-dimethyl-2-furanmethanamine (1.51 g) was heated at 140° for 4 h. The residue was chromatographed (silica/ethyl acetate-methanol, 1:1) to give the title compound (0.85 g) as a semi-solid T.L.C. (silica/methanol - 0.88 ammonia, 79:1) Rf. 0.58.

Analysis, Found: C, 63.6; H, 6.1; N, 14.9;. $C_{24}H_{27}N_5O_2S\frac{1}{4}H_2O$ requires: C, 63.5; H, 6.1; N, 15.4%.

EXAMPLE 8

2-[[2[[[5-[(Dimethylamino)methyl]-2-furanyl]methyl]-thio]ethyl]amino]-5-phenyl-4(3H)-pyrimidinone

A. 2-(Methylthio)-5-phenyl-4(3H)-pyrimidinone

To a stirred suspension of finely divided sodium (2 g) in dry ether (50 ml) was added a mixture of ethylphenyl acetate (14.2 g) and ethyl formate (7.6 g) during 3 h. After 12 h. evaporation of the ether gave an oily residue which was dissolved in water (100 ml) containing S-methylisothiouronium sulphate (12.02 g). A solution of sodium hydroxide (3.46 g) in water (20 ml) was added and after 6 h. at 0°, the pH of the solution was adjusted to 6 with acetic acid. The solid which separated was crystallised from ethanol to yield the title compound (1.8 g) m.p. 252°–254°.

T.L.C. (silica/diethyl ether) Rf. 0.66.

B. 2-[[2-[[[5-[(Dimethylamino)methyl]-2-furanyl]methyl]-thio]ethyl]amino]-5-phenyl-4(3H)-pyrimidinone A mixture of 2-(methylthio)-5-phenyl-4(3H)-pyrimidinone (1.09 g) and 5-[[(2-aminoethyl)thio]methyl]-N,N-dimethyl-2-furanmethanamine (2.14 g) was heated at 140° for 4 h. The cooled residue was chromatographed (silica/ethyl acetate-methanol, 1:1) to give a product which was crystallised from methyl acetate-light petroleum (b.p. 60°–80°) yielding the title compound (1.52 g) m.p. 116°–118°.

T.L.C. (silica/methanol) Rf. 0.33.

EXAMPLE 9

2-[[2-[[[5-[(Dimethylamino)methyl]-2-furanyl]methyl-thio]ethyl]amino-5-[(1H-indol-3-yl)methyl]-4(3H)-pyrimidinone

A. 5-[(1H-Indol-3-yl)methyl]-2-mercapto-4(3)-pyrimidinone

To a stirred suspension of finely divided sodium (1 g) in dry ether (30 ml) was added a solution of 3-indolepropanoic acid, ethyl ester (9.5 g) and ethyl formate (4 ml) in dry ether (60 ml). After stirring at room temperature for 2 days, the ether was evaporated and a solution of the residue and thiourea (3.35 g) in ethanol (40 ml) was refluxed for 6 h. Evaporation of the solvent gave a residue which was dissolved in water (100 ml) and acidified with acetic acid. The solid which separated was crystallised from ethanol to give the title compound (1.17 g) m.p. 219°–219.5°.

T.L.C. (silica/methanol) Rf. 0.5.

B. 5-(1H-Indol-3-yl)methyl]-2-(methylthio)-4(3H)-pyrimidinone

A solution of sodium hydroxide (0.2 g), 5-[(1H-indol-3-yl)methyl]-2-mercapto-4(3HO-pyrimidinone (1 g) and methyl iodide (0.68 g) in water (1 ml) and ethanol (40 ml) was heated with stirring at 60° for 1.5 h. Evaporation of half of the solvent yielded a solid which was filtered, washed with water and dried to give the title compound (0.3 g).

T.L.C. (silica/methanol) Rf. 0.77.

N.M.R. τ (CDCl$_3$d$^6$DMSO)-0.4(1H, br, NH), 2.30–3.00 (7H, m, 6CH and NH), 6.12 (2H, brs, CH$_2$), 7.60 (3H, s, CH$_3$).

C.
2-[[2-[[[5-[(Dimethylamino)methyl]-2-furanyl]methyl]thio]ethyl]amino]-5-[(1H-indol-3-yl)methyl]-4(3H)-pyrimidinone A mixture of 5-[(1H-indol-3-yl)methyl]-2-(methylthio)-4(3H)-pyrimidinone (0.3 g) and 5-[[2-aminoethyl)thio]methyl]-N,N-dimethyl-2-furanmethanamine (0.5 g) was heated at 120° for 8 h. Column chromatography (silica/methanol) on the residue yielded the title compound (0.22 g) as an amber gum.

T.L.C. (silica/methanol - 0.88 ammonia, 79:1) Rf. 0.63.

Analysis, Found: C, 61.8; H, 6.4; N, 15.3; $C_{23}H_{27}N_5O_2S\frac{1}{2}H_2O$ requires: C, 61.9; H, 6.3; N, 15.7%.

EXAMPLE 10
5-(3-Phenylpropyl)-2[[3-[3-[(1-piperidinyl)methyl]phenoxy propyl]amino]-4(3H)-pyrimidinone

A. 1,2-Dihydro-5-(3-phenylpropyl)-2-thioxo-4(3H) pyrimidinone

To a stirred suspension of finely divided sodium (2.3 g) in dry ether (50 ml) was added a mixture of 5-phenylvaleric acid, ethyl ester (20.6 g) and ethyl formate (8.14 g) in dry ether (100 ml) during 2 h. After 12 h. the solvent was evaporated and a mixture of the residue and thiourea (8.36 g) in ethanol (100 ml) was refluxed for 6 h. Evaporation of the ethanol gave a solid which was dissolved in water (100 ml) and acidified with acetic acid. The solid which separated was crystallised from water to give the title compound (4.5 g), m.p. 180°-182°.

T.L.C. (silica/light petroleum b.p. 60°-80° ethyl acetate, 5:2) Rf. 0.15.

B. 2-(Methylthio)-5-(3-phenylpropyl-4(3H)-pyrimidinone

Dimethyl sulphate (1.89 g) was added to a stirred solution of 1,2-dihydro-5-(3-phenylpropyl)-2-thioxo-4(3H)-pyrimidinone (3.69 g) and potassium hydroxide (0.84 g) in water (50 ml) at 0°. The solid which separated was crystallised from aqueous ethanol to give the title compound (1.2 g), m.p. 136°-138°.

T.L.C. (silica/light petroleum b.p. 60°-80° ethyl acetate, 5:2) Rf. 0.15.

C. 5-(3-Phenylpropyl)-2-[[3-[3-[(1-piperidinyl)methyl]phenoxy]propyl]amino]-4(3H)-pyrimidinone A mixture of 2-(methylthio)-5-(3-phenylpropyl)-4(3H)-pyrimidinone (0.52 g) and 3-[3-[(1-piperidinyl)methyl]phenoxy]propanamine (1.056 g) was heated at 140° for 4 h. The residue was chromatographed (silica/methanol-ethyl acetate 1:1) and the oily product titrated with light petroleum (b.p. 60°-80°) to give the title compound (0.18 g), m.p. 104°-108°.

T.L.C. (silica/methanol - 0.88 ammonia, 79:1) Rf. 0.68.

EXAMPLE 11
5-Butyl-2-[[3-[3-[(1-piperidinyl)methyl]phenoxy]propyl]amino]-4(3H)- pyrimidinone

A. 5-Butyl-2-(methylthio)-4(3H)-pyrimidinone

Methyl iodide (2.74 g) was added to a stirred solution of 5-butyl-2,3-dihydro-2-thioxo-4(1H)-pyrimidinone (3.5 g) and sodium hydroxide (0.78 g) in water (10 ml) and ethanol (20 ml) at room temperature and heated at 70° for 45 minutes. The solid which separated on standing was filtered and washed with ethanol and water to give the title compound (0.95 g) m.p. 138°-140.5°.

TLC (Silica/ethyl acetate) Rf 0.73.

B. 5-Butyl-2-[[3-[3-[(1-piperidinyl)methyl]phenoxy]propyl]amino]-4(3H)-pyrimidinone A mixture of 5-butyl-2-(methylthio)-4(3H)-pyrimidinone (0.85 g) and 3-[3-[(1-piperidinyl)methyl]phenoxy]propanamine (1.1 g) was heated at 98°-100° for 6 hours and 140° for 2 hours. The residue was chromatographed (silica/methanol) to give an oil which solidified yielding the title compound (1.41 g) m.p. 105°-105.5°.

TLC (silica/methanol) Rf 0.31.

EXAMPLE 12
Pharmaceutical Compositions

(a) TABLETS

|  | mg/tablet | mg/tablet |
|---|---|---|
| Active ingredient | 50.0 | 100.0 |
| Microcrystalline Cellulose B.P.C. | 149.00 | 298.00 |
| Magnesium Stearate B.P. | 1.00 | 2.00 |
| Compression weight | 200.00 | 400.00 |

The active ingredient is sieved through a 250 μm sieve, blended with the excipients and compressed using 8.5 mm and 10.0 mm diameter punches for the 50 and 100 mg. strengths respectively. Tablets of other strengths may be prepared by increasing the compression weight and using punches to suit.

The tablets may be film coated with suitable film forming materials, e.g. methyl cellulose, or hydroxypropylmethyl cellulose, using standard techniques. Alternatively the tablets may be sugar coated.

(b) CAPSULES

|  | mg/capsule |
|---|---|
| Active ingredient | 50.00 |
| *STA-RX 1500 | 49.50 |
| Magnesium stearate B.P. | 0.50 |

*A form of directly compressible starch supplied by Colorcon Ltd. Orpington, Kent.

The active ingredient is sieved through a 250 μm sieve and belnded with the other materials. The mix is filled into No. 3 hard gelatin capsules using a suitable filling machine. Other doses may be prepared by increasing the fill weight and if necessary changing the capsule size to accommodate the increase.

(c) SUSTAINED RELEASE TABLETS

|  | mg/tablet |
|---|---|
| Active ingredient | 200.00 |
| + Cutina HR | 50.00 |
| Lactose B.P. | 247.5 |
| Magnesium stearate B.P. | 2.50 |

+ Cutina HR is a grade of microfine hydrogenated castor oil supplied by Sipon Products Ltd. London.

The active ingredient is sieved through a 250 μm sieve and blended with the Cutina HR and lactose. The mixed powders are moistened with Industrial Methylated Spirits 740.P., granules are made, dried, screened and blended with the Magnesium stearate The lubricated granules are compressed using 10.5 mm punches to produce tablets with a hardness of not less than 10Kp (Schleuniger hardness tester).

(d) SYRUP

|  | mg/5 ml dose |
|---|---|
| Active ingredient | 50.0 mg |
| Sucrose B.P. | 2750.0 mg |
| Glycerine B.P. | 500.0 mg |
| Buffer | |
| Flavour | |
| Colour | as required |
| Preservative | |
| Distilled Water to | 5.0 ml |

The active ingredient, buffer, flavour colour and preservative are dissolved in some of the water, and the glycerine is added. The remainder of the water is heated to 80° C. and the sucrose is dissolved in this and cooled. The two solutions are combined, adjusted to volume and mixed. The syrup produced is clarified by filtration.

(e) INJECTION FOR INTRAVENOUS ADMINISTRATION

|  | % w/v |
|---|---|
| Active ingredient | 0.50 |
| Water for injections B.P. to | 100.00 |

Sodium chloride may be added to adjust the tonicity of the solution and the pH may be adjusted to that of maximum stability using either dilute acid or alkali.

The solution is prepared, clarified and filled under nitrogen into appropriate sized ampoules sealed by fusion of the glass. The injection is sterilised by heating in an autoclave using one of the acceptable cycles. Alternatively the solution may be sterilised by filtration and filled into sterile ampoules under aseptic conditions.

EXAMPLE 13

2-[[2-[[[5-(Ethylmethylamino)methyl]-2-thienyl]methyl]thio]ethyl]amino]-5-(3-pyridinyl)methyl]-4(3H)-pyrimidinone A mixture of 5-[[(2-aminoethyl)thio]methyl]-N-ethyl-N-methyl-2-thiophenemethanamine (0.87 g) and 2-(methylthio)-5-[(3-pyridinyl)methyl]-4(3H)-pyrimidinone (0.7 g) was heated at 140° for 6 hours. The residue was purified by column chromatography (silica/methanol) to give an oil which solidified on trituration with ether yielding the title compound (0.95 g), m.p. 117°–118°. TLC (silica/methanol) Rf 0.33.

We claim:

1. Compounds of the formula (1):

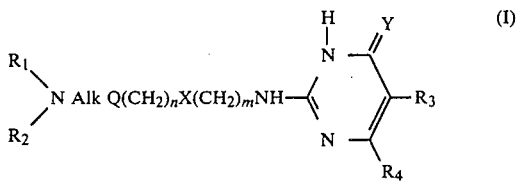

and physiologically acceptable acid addition salts, and hydrates thereof, in which $R_1$ and $R_2$ which may be the same or different, each represent hydrogen, $C_1$-$C_6$ alkyl, $C_3$-$C_8$ cycloalkyl, $C_3$-$C_6$ alkenyl, $C_3$-$C_6$ alkynyl, ar$C_1$-$C_6$ alkyl or $C_1$-$C_6$ alkyl substituted by hydroxy, $C_1$-$C_3$ alkoxy, amino, $C_1$-$C_4$ alkylamino or di-$C_1$-$C_3$ alkylamino or $R_1$ and $R_2$ together with the nitrogen atom to which they are attached form a saturated monocyclic 5 to 7 membered heterocyclic ring which may contain the further heterofunction —O—;

Alk represents a straight alkylene chain of 1 to 4 carbon atoms;

Q represents a benzene ring in which incorporation into the rest of the molecule is through bonds at the 1- and 3- or 1- and 4-positions;

X represents —$CH_2$—, —O— or —S—;

n represents zero or 1;

m represents 2, 3 or 4;

Y represents =O or =S;

$R_3$ represents hydrogen in which case $R_4$ represents methyl or $R_3$ represents —$(CH_2)_p$—V$(CH_2)_q$Ar, phenyl or $C_1$-$C_6$ alkyl in which case $R_4$ represents hydrogen;

V represents —$CH_2$—, —O— or —S—;

p represents zero, 1, 2 or 3;

q represents zero, 1, 2 or 3; the sum of p+q being 3 or less;

Ar represents phenyl, substituted phenyl which is substituted by one or more substituents selected from the group consisting of $C_{1-3}$ alkyl, $C_{1-2}$ alkoxy $C_{1-3}$ alkyl, hydroxy, $C_{1-3}$ alkoxy, methylenedioxy, halogen, trifluoromethyl and di-$C_{1-3}$-alkylamino; naphthyl, pyridyl, furanyl, thienyl, thiazolyl, oxazolyl, indolyl, quinolyl or isoquinolyl.

2. Compounds according to claim 1 in which $R_1R_2N$ represent an $C_1$-$C_6$ alkylamino or di-$C_1$-$C_6$-alkylamino group or a 5 to 7-membered ring without a further heterofunction.

3. Compounds according to claim 1 in which: n is 1, X is sulphur and m is 2 or 3, or n is 1, X is oxygen and m is 3 or 4, or n is zero, X is oxygen and m is 3.

4. Compounds according to claim 1 in which Y is oxygen.

5. Compounds according to claim 1 in which $R_4$ is hydrogen and $R_3$ represents the group $(CH_2)_pV(CH_2)_q$Ar where p is 0, 1 or 2, V is $CH_2$ or oxygen and q is 0 or 1.

6. Compounds according to claim 1 in which Ar is 2, 3 or 4-pyridyl, phenyl monosubstituted by $C_1$-$C_6$ alkoxy or by dialkylamino, or 3-quinolyl.

7. Compounds according to claim 1 in which Q is 1,3-benzene and Alk is $CH_2$.

8. Compounds according to claim 1 in which $R_4$ is hydrogen, $R_3$ represents the group $(CH_2)_pV(CH_2)_q$Ar and Ar is phenyl substituted by $C_{1-3}$ alkoxymethyl.

9. Compounds according to claim 8 in which p is 2, q is zero and V is oxygen.

10. Compounds according to claim 1 in which $R_4$ is hydrogen $R_3$ represents the group $(CH_2)_pV(CH_2)_q$Ar and Ar is 3-indolyl.

11. Compounds according to claim 1 in which $R_4$ is hydrogen and $R_3$ represents the group $(CH_2)_pV(CH_2)_q$Ar where pnO, qnO and V is $CH_2$.

12. Compounds according to claim 1 in which $R_1R_2N$ is $(CH_3)_2N$ or pyrrolidino; Alk is $CH_2$; $R_4$ is hydrogen; $R_3$ is $(CH_2)_pV(CH_2)_q$Ar; Ar is 3-pyridyl or 4-pyridyl; Y is oxygen; V is $CH_2$; p and q are both zero; and Q is 1,3-benzene and n is zero, m is 3 and X is oxygen.

13. Compounds according to claim 1 which are

2-[[3-[3-[(dimethylamino)methyl]phenoxy]propyl-]amino]-5-[(3-pyridinyl)methyl]-4(3H)-pyrimidinone 2-[[3-[3-[(1-pyrrolidinyl)methyl]phenoxy]propyl-]amino]-5-[(3-pyridinyl)methyl]-4(3H)-pyrimidinone 5-phenylmethyl-2-[[3-[3-[(1-pyrrolidinyl)methyl]-phenoxy]propyl]amino]-4(3H)pyrimidinone 2-[[3-[3-[(1-piperidinyl)methyl]phenoxy]propyl-]amino]-5-[(3-pyridinyl)methyl]-4(3H)-pyrimidinone and their physiologically acceptable salts.

14. A pharmaceutical composition for the treatment of conditions mediated through $H_2$-receptors comprising an effective amount of a compound as defined in claim 1 together with at least one pharmaceutically acceptable carrier or diluent.

15. A pharmaceutical composition according to claim 14 in which the compound is in the form of a physiologically acceptable salt.

16. A method of treating a condition mediated through histamine $H_2$-receptors which comprises administering to a patient an effective amount of a compound as defined in claim 1 to relieve said condition.

17. Compounds of formula (I) as defined in claim 1 and physiologically acceptable acid addition salts, and hydrates thereof, in which $R_1$ and $R_2$ which may be the same or different each represent hydrogen, $C_1$-$C_6$-alkyl, $C_3$-$C_6$-cycloalkyl, $C_3$-$C_6$-alkenyl, ar$C_1$-$C_6$-alkyl or $C_1$-$C_6$-alkyl substituted by $C_{1-3}$ alkoxy, $C_{1-3}$ alkylamino or di-$C_{1-3}$ alkyl amino, or $R_1$ and $R_2$ together with the nitrogen atom to which they are attached form a piperidino, pyrrolidino or morpholino group;

Alk represents $CH_2$;

$R_3$ represents —$(CH_2)_p V(CH_2)_q$Ar and $R_4$ represents hydrogen;

Ar represents pyridyl, furanyl, thienyl, thiazolyl, oxazolyl, indolyl, quinolyl or isoquinolyl, phenyl, substituted phenyl which is substituted by one or more substituents selected from the group consisting of $C_{1-3}$ alkyl, hydroxy, $C_{1-3}$ alkoxy, methylenedioxy, halogen, trifluoromethyl and di-$C_{1-3}$ alKylamino and Q, X, V, n, m, p, q and Y are as defined in claim 1.

18. The compound of 2[3-[3-[(dimethylamino)methyl]phenoxy]propylamino]-5-[(3-pyridinyl)methyl]-4(3-H)-pyrimidone.

19. Compounds of the formula (I):

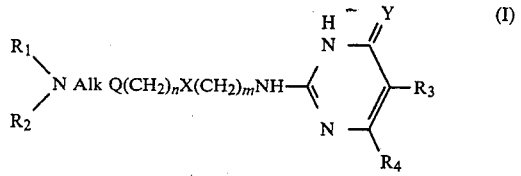

and physiologically acceptable salts thereof, in which $R_1$ and $R_2$, which may be the same or different, each represents hydrogen, $C_{1-6}$ alkyl or $R_1$ and $R_2$ together with the nitrogen atom to which they are attached form a N-piperidino or a N-pyrrolidino group;

Alk represents a straight alkylene chain of 1 to 4 carbon atoms;

Q represents a benzene ring in which incorporation into the rest of the molecule is through bonds at the 1- and 3- or 1- and 4-positions;

X represents —$CH_2$—, —O— or —S—;

n represents zero or 1;

m represents 2 or 3;

Y represents =O;

$R_3$ represents —$(CH_2)_p$—$V(CH_2)_q$ Ar;

$R_4$ represents hydrogen;

V represents —$CH_2$—, —O— or —S— p represents zero, 1, 2 or 3;

q represents zero, 1, 2 or 3; the sum of p+q being 3 or less;

Ar represents phenyl, substituted phenyl which is substituted by one or more substituents selected from the group consisting of $C_{1-3}$ alkyl, hydroxy, $C_{1-3}$ alkoxy, methylenedioxy, halogen, trifluoromethyl and di-$C_{1-3}$ alkylamino; naphthyl, pyridyl, furanyl, thienyl, thiazolyl, oxazolyl, quinolyl or isoquinolyl.

20. A method of treating a condition mediated through histamine $H_2$-receptors which comprises administering to a patient an effective amount of a compound of the formula (I):

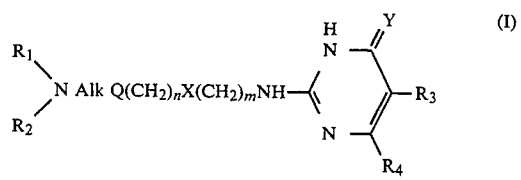

and physiologically acceptable acid addition salts thereof, in which $R_1$ and $R_2$, which may be the same or different, each represents hydrogen, $C_{1-6}$ alkyl or $R_1$ and $R_2$ together with the nitrogen atom to which they are attached form a N-piperidino or a N-pyrrolidino group;

Alk represents a straight alkylene chain of 1 to 4 carbon atoms;

Q represents a benzene ring in which incorporation into the rest of the molecule is through bonds at the 1- and 3- or 1- and 4-positions;

X represents —$CH_2$—, —O— or —S—;

n represents zero or 1;

m represents 2 or 3

Y represents =O;

$R_3$ represents —$(CH_2)_p$—$V(CH_2)_q$ Ar;

$R_4$ represents hydrogen;

V represents —$CH_2$—, —O— or —S—;

p represents zero, 1, 2 or 3;

q represents zero, 1, 2 or 3; the sum of p+q being 3 or less;

Ar represents phenyl, substituted phenyl which is substituted by one or more substituents selected from the group consisting of $C_{1-3}$ alkyl, hydroxy, $C_{1-3}$ alkoxy, methylenedioxy, halogen, trifluoromethyl and di-$C_{1-3}$ alkylamino; naphthyl, pyridyl, furanyl, thienyl, thiazolyl, oxazolyl, quinolyl or isoquinolyl to relieve said condition.

21. A pharmaceutical composition for the treatment of conditions mediated through $H_2$-receptors comprising an effective amount of a compound of the formula (1):

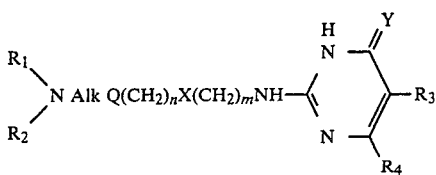

and physiologically acceptable acid addition salts thereof, in which

R$_1$ and R$_2$, which may be the same or different, each represents hydrogen, C$_{1-6}$ alkyl or R$_1$ and R$_2$ together with the nitrogen atom to which they are attached form a N-piperidino or a N-pyrrolidino group;

Alk represents a straight alkylene chain of 1 to 4 carbon atoms;

Q represents a benzene ring in which incorporation into the rest of the molecule is through bonds at the 1- and 3- or 1- and 4-positions;

X represents —CH$_2$—, —O— or —S—;

n represents zero or 1;

m represents 2 or 3;

Y represents =O;

R$_3$ represents —(CH$_2$)$_p$—V(CH$_2$)$_q$Ar;

R$_4$ represents hydrogen;

V represents —CH$_2$—, —O— or —S—;

p represents zero, 1, 2 or 3;

q represents zero, 1, 2 or 3; the sum of p+q being 3 or less;

Ar represents phenyl, substituted phenyl which is substituted by one or more substituents selected from the group consisting of C$_{1-3}$ alkyl, hydroxy, C$_{1-3}$ alkoxy, methylenedioxy, halogen, trifluoromethyl and di-C$_{1-3}$ alkylamino; naphthyl, pyridyl, furanyl, thienyl, thiazolyl, oxazolyl, quinolyl or isoquinolyl and a pharmaceutically acceptable diluent or carrier.

* * * * *